(12) United States Patent
Boebel et al.

(10) Patent No.: US 8,568,423 B2
(45) Date of Patent: Oct. 29, 2013

(54) UTERUS MANIPULATOR

(75) Inventors: Manfred Boebel, Bauschlott (DE);
Bernd Claus Weber, Karlsruhe (DE);
Eugenio Solima, Milan (IT)

(73) Assignee: Richard Wolf GmbH, Knittlingen (DE)

( * ) Notice: Subject to any disclaimer, the term of this patent is extended or adjusted under 35 U.S.C. 154(b) by 128 days.

(21) Appl. No.: 12/958,725

(22) Filed: Dec. 2, 2010

(65) Prior Publication Data

US 2011/0130769 A1 Jun. 2, 2011

(30) Foreign Application Priority Data

Dec. 2, 2009 (DE) .......................... 10 2009 056 705

(51) Int. Cl.
*A61B 17/42* (2006.01)
(52) U.S. Cl.
USPC .......................................................... 606/119
(58) Field of Classification Search
USPC .......... 606/119, 120–126; 604/30, 34, 35, 27, 604/158, 264
See application file for complete search history.

(56) References Cited

U.S. PATENT DOCUMENTS

| | | | | |
|---|---|---|---|---|
| 5,209,754 A | * | 5/1993 | Ahluwalia | 600/207 |
| 5,217,466 A | * | 6/1993 | Hasson | 606/119 |
| 5,295,984 A | * | 3/1994 | Contente et al. | 604/317 |
| 5,394,863 A | * | 3/1995 | Sanford et al. | 600/199 |
| 5,520,698 A |   | 5/1996 | Koh | |
| 5,928,249 A | * | 7/1999 | Saadat et al. | 606/119 |
| 5,951,465 A | * | 9/1999 | Schiff et al. | 600/224 |
| 2006/0004398 A1 | * | 1/2006 | Binder et al. | 606/191 |
| 2010/0106163 A1 | * | 4/2010 | Blair et al. | 606/119 |

FOREIGN PATENT DOCUMENTS

DE 85 29 364 U1 10/1986
DE 195 43 576 A1 6/1997

OTHER PUBLICATIONS

German Examination Report issued on Jul. 2, 2010 in the German Application 10 2009 056 705.4.

* cited by examiner

*Primary Examiner* — Tuan V Nguyen
(74) *Attorney, Agent, or Firm* — Panitch Schwarze Belisario & Nadel LLP

(57) ABSTRACT

A uterus manipulator includes a shank, in which a hollow probe is guided, whose distal end section is envisaged and designed for introduction into a uterus through the cervical canal. A handle is provided on the proximal side. A distally open bell and a vaginal seal, arranged proximally displaced thereto, as well as a suction channel which connects to at least one suction opening in the distal end section, are provided for receiving a cervix. The bell is designed as a suction bell, wherein at least one suction channel runs into the bell.

15 Claims, 5 Drawing Sheets

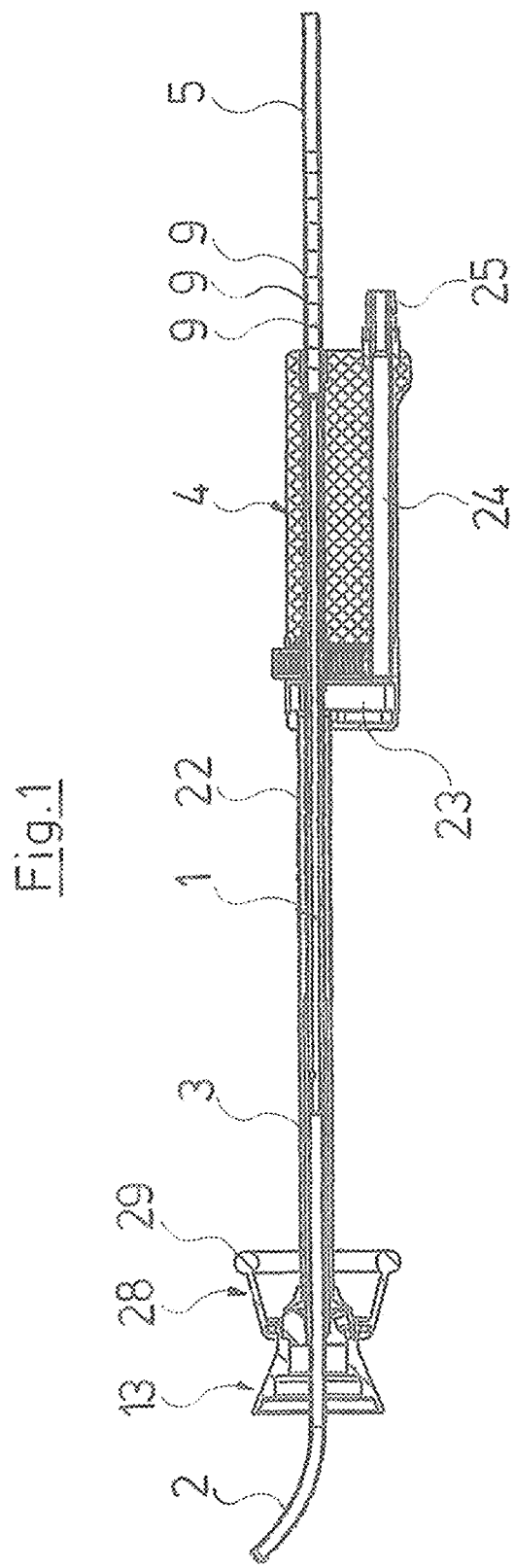

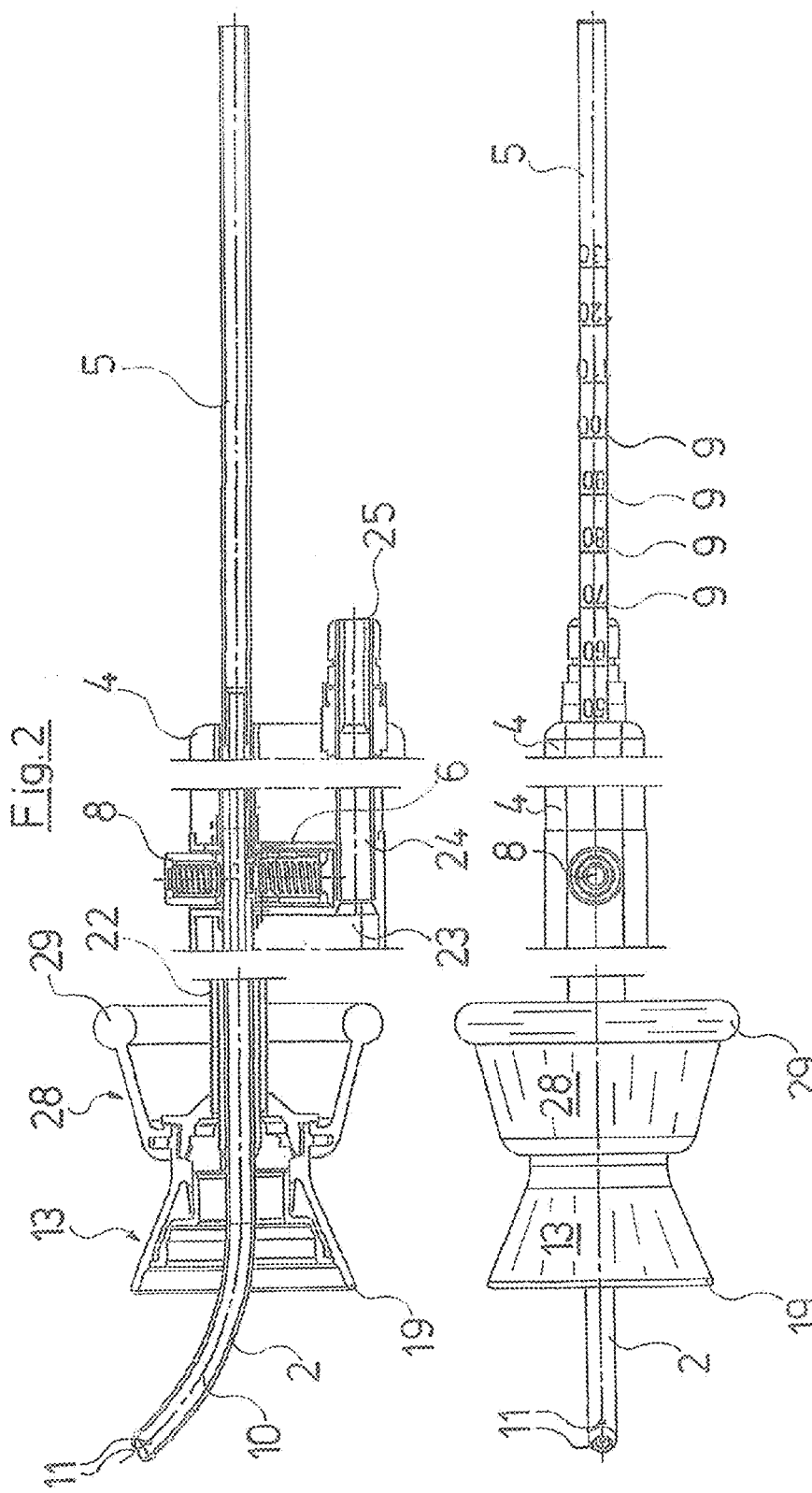

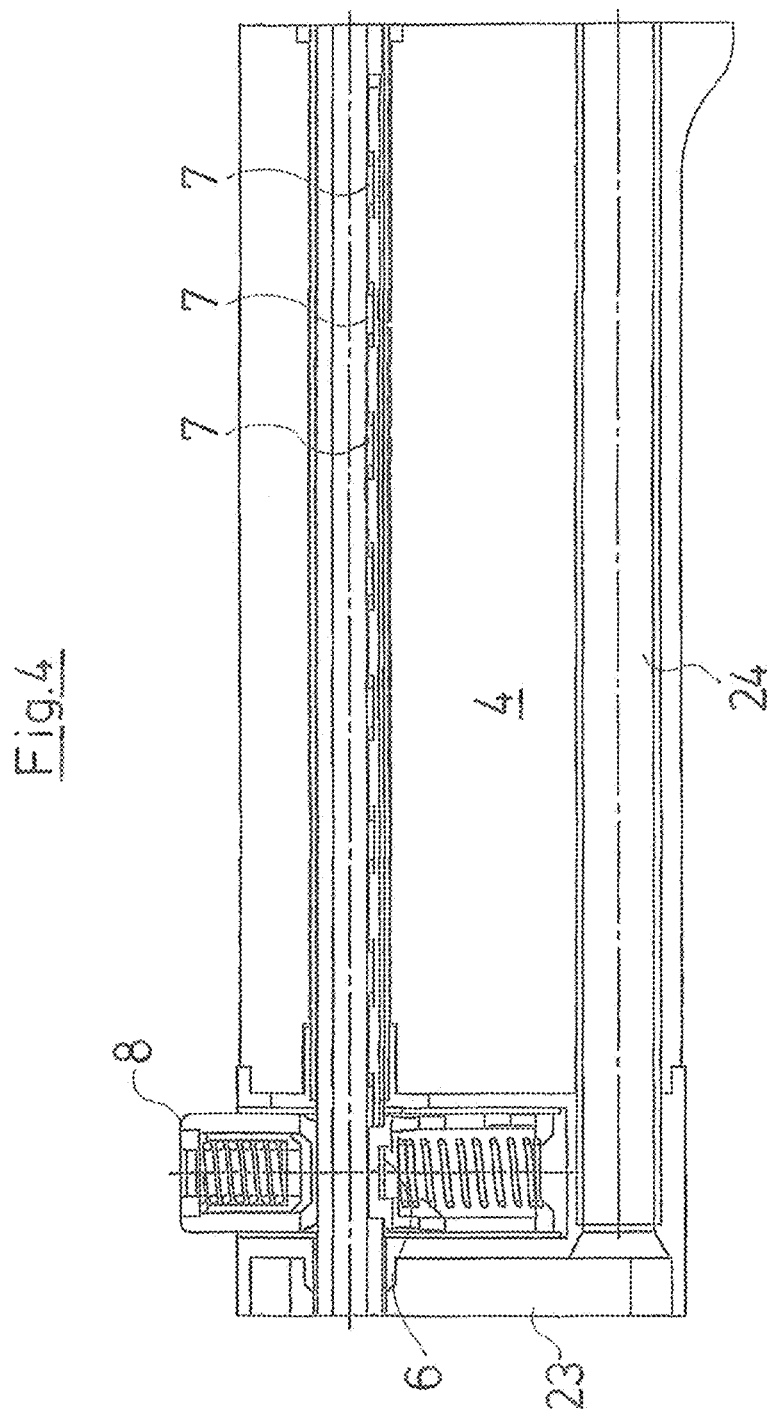

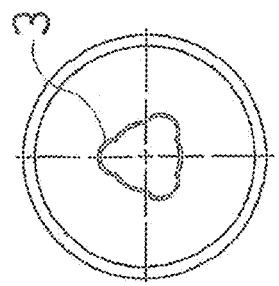
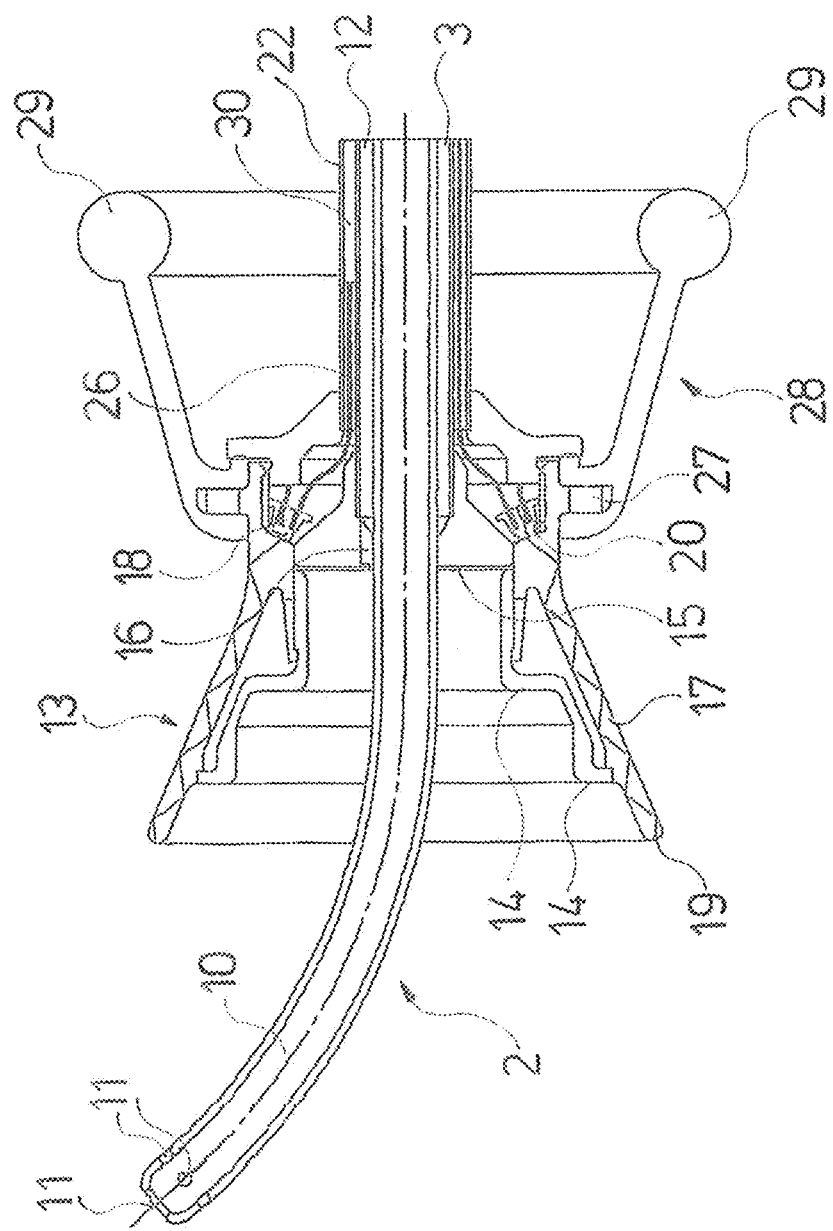

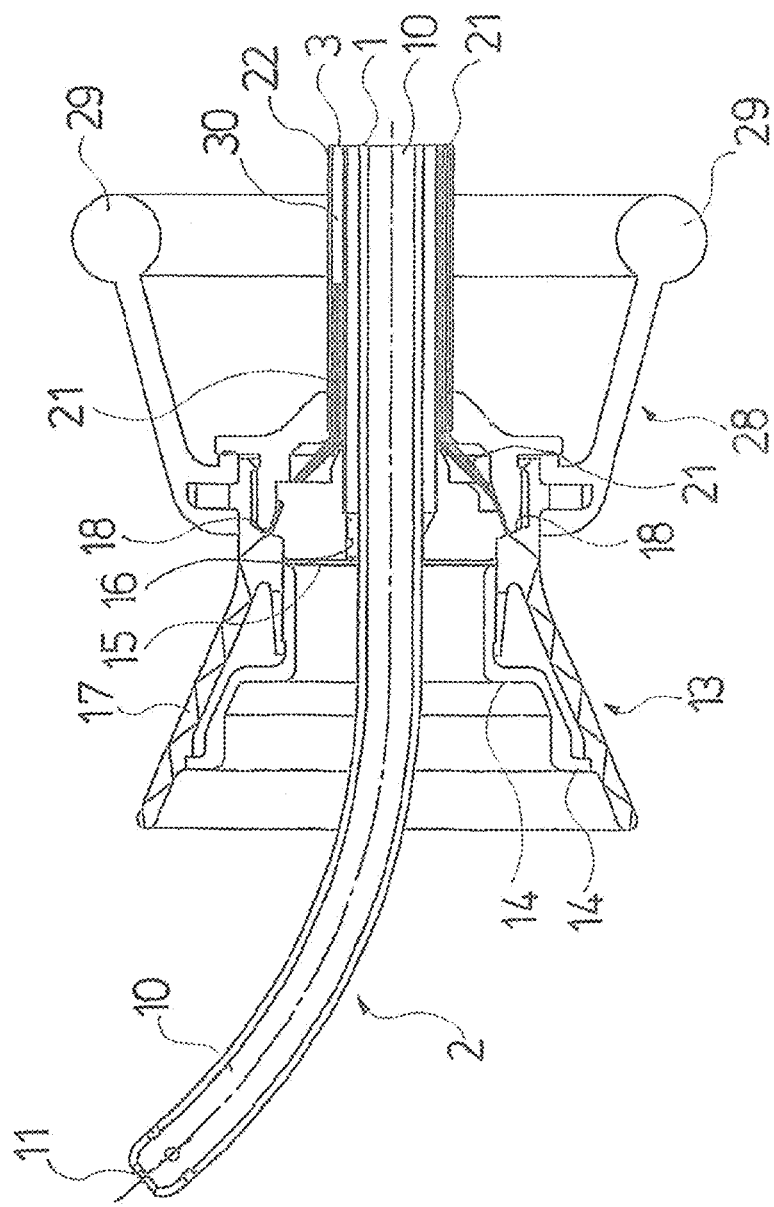

UTERUS MANIPULATOR

BACKGROUND OF THE INVENTION

The invention relates to a uterus manipulator, in particular for laparoscopically assisted vaginal hysterectomy.

With the combined operative removal of the uterus carried out laparoscopically and through the vagina (LAVH—laparoscopically assisted vaginal hysterectomy), one requires an instrument set which among other things comprises a uterus manipulator, with which the uterus from the outside, may be led through the vagina by a probe introduced through the cervical canal. Such a uterus manipulator is known for example from U.S. Pat. No. 5,520,698. This instrument, additionally to the probe, yet comprises a bell which is open at the distal end and which serves for receiving the cervix and improves the leading of the uterus through the instrument. The bell is provided with lateral openings. A vaginal seal is provided on the proximal side of the bell and at a distance to it and is formed by an inflatable balloon ring, which is to be applied in a sealing manner onto the vaginal wall and ensures that after severing the rear fornix, the pneumoperitoneum is maintained, in order to counteract a collapse of the abdomen.

Such uterus manipulators are considered as part of the prior art and are provided by various manufacturers in different designs. In this regard, it is further considered as part of the prior to design the probe as a hollow probe and thus to carry out a suctioning of intrauterine cells during the operation to avoid the spread of carcinogenic cells.

However, it has been found that this intrauterine cell suctioning is inadequate, in particular with the previously described instrument, with which a balloon is likewise inflated for fixing the probe there within the uterus. The inflating of this inner balloon is, however, necessary in order to ensure a secure retention of the probe within the uterus and thus to ensure a secure leading of the uterus from the outside by the manipulator.

BRIEF SUMMARY OF THE INVENTION

Against this background, it is an object of the invention to improve a uterus manipulator of the known type, with regard to its functionality and handling, as well as in particular to avoid the previously mentioned disadvantages.

According to the invention, this object is achieved by the features specified in claim 1. Advantageous designs of the invention are specified in the dependent claims, the subsequent description as well as the drawing.

The uterus manipulator according to the invention, which in particular is envisaged for laparoscopically assisted vaginal hysterectomy, comprises a shank as well as a distal end section, which is envisaged and designed for introduction into a uterus through the cervical canal. It further comprises a proximal handle as well as a distally open bell for receiving a cervix. A vaginal seal is arranged proximally displaced to this bell. The uterus manipulator furthermore comprises at least one suction channel, which is conductively connected to at least one suction opening in the distal end section. According to the invention, the bell is here designed as a suction bell. For this, the uterus manipulator comprises a suction channel which runs out into the bell. Here, according to the invention, the vaginal seal is formed by a sealing bell, which is open proximally and whose peripheral edge is designed for the sealed bearing on the vaginal wall. According to the invention, the suction bell and the sealing bell are designed as a unit or at least part of a unit releasably fastened on the shank.

The basic concept of the solution according to the invention is to provide a suction bell, thus a suction bell which is subjected to a vacuum via a suction channel and a suction conduit connecting thereto, so that a suctioning of any carcinogenic cells may not only be effected out of the uterus via the suction opening in the distal end section, but also externally in the region of the portio, by the suction bell. Here, the suction bell according to the invention not only serves for the cell suctioning in the region of the portio, but moreover also the fixation on the uterus manipulator, so that a mechanical anchoring of the distal end section within the uterus may be done away with. Thus, with the uterus manipulator according to the invention, one may apply pulling forces from the outside, without there being the danger of the distal end section sliding out of the cervical canal. Moreover, it is ensured that even the cells which get between the distal end section of the instrument and the cervical canal, are suctioned through the suction channel connecting to the suction bell and thus do not get to the region of the vagina.

Due to the fact that the vaginal seal is formed by a sealing bell, which is open proximally and whose peripheral edge is designed for the sealed bearing on the vaginal wall, a common attachment of the components on the instrument is possible, but the required distance is simultaneously formed, this distance being required so that the sealing effect is maintained after severing the rear fornix.

Due to the fact that the suction bell and the sealing bell, which forms the vaginal seal, form a unit (or construction unit) or at least part of a unit, which is releasably fastened on the shank, this unit may be designed as a disposable article and kept ready in a sterile package, and thus is only connected to the instrument directly before use. Here, it is particularly advantageous if only one common connection of this unit to the shank is provided, since this simplifies the handling.

Typically, with regard to the distal end section, it is the case of the end section of a hollow probe. Here, in the simplest case, the hollow probe may be formed by the shank itself. Typically and preferred however, the hollow probe is movably guided within the instrument shank.

According to one advantageous further embodiment of the invention, the suction bell at its inner side, thus on the inner periphery, comprises at least one, preferably several graduations. The graduation serves for adapting the instrument to different portio sizes, so that it is ensured that the portio bears on the suction bell over the whole periphery in a tight and mechanically stable manner.

It is particularly advantageous if the suction bell comprises a distal, peripheral edge, and illumination means are provided for illuminating this edge. Here, the bell is usefully of a transparent material, so that it may be attached under visual control. The illumination of the peripheral edge, according to embodiments of the invention, may either be effected by illumination means, typically light diodes, attached in the region of the bell, or instead by fiber-optics which connect to the suction bell and are supplied with light from the proximal instrument end via a light source.

The illumination of this peripheral edge, although capable of being advantageous for handling the manipulator, in particular for introducing the distal end section into the cervical canal, has as its significant advantage the fact that the rear fornix is illuminated where it is to be severed by a peripheral cut, so that on the one hand the operator has a better orientation and on the other hand vessels or the like, which lie there, are also visible. For this, the suction bell should usefully consist of a light-conducting material, preferably of a clear, transparent glass or plastic.

Here, it has been found to be particularly advantageous if the suction bell at the outer periphery is designed in a truncated-cone-like manner, and is stepped several times on the inner periphery, and the light impingement is effected on an end-face close to the shank-side inner periphery. Here, the multiple stepping of the inner side of the suction bell serves for the adaptation to anatomical size differences, whereas the outer shape essentially serves for transmitting the light by total reflection on the walls from the proximal end-face close to the shank-side inner periphery, towards the distal-side ring. The utilization of the total reflection is particularly advantageous, but not compelling, and a leading of light via a fiber-optic or other suitable designs of the bell wall may also be effected in this region.

With regard to the functionality, it is particularly advantageous if the suction bell is formed by a component which is as inherently rigid and stable as possible, whereas the vaginal seal at least in the peripheral region should be designed as soft-elastically as possible, at least in the peripheral region. Here, the suction bell may advantageously be designed as a plastic injection molded part. It is particularly useful if not only the suction bell, but also the part of the unit which serves for fastening (which may of course also be part of the bell), as well as optionally even the inner part of the sealing bell, is designed as a plastic injection molded part, and the outer part of the sealing bell, at least the vaginal seal, is manufactured of a soft-elastic part, e.g., a silicone part. The components may be connected with a material fit into a unit, but a positive-fit connection in the manner of a bead-and-groove connection is also conceivable, as is known per se with seals, or a combination of these.

Advantageously, according to a further embodiment of the invention, a hollow probe is guided in the shank of the instrument in a rotationally fixed, but axially displaceable manner, and this hollow probe comprises the distal end section for introduction into the cervical canal and may be fastened in at least two different axial positions with respect to the shank and/or the proximal handle. The part of the hollow probe, which projects beyond the shank, forms the distal end section which is provided for introduction into the cervical canal. In order here to adapt the instrument to the anatomical size conditions, the hollow probe is axially displaceable and arranged fixable in different positions, in order thus to be able to adapt the length of the distal end section in an individual manner. Here, the hollow probe is arranged within the instrument in a rotationally fixed manner, in order to be able to carry out the manipulation required with the operation, not only in the axial direction, but also in the rotational direction about the axis.

Usefully, the suction bell, preferably the whole unit with the suction bell and vaginal seal, is fastened close to the distal shank end on this, for example by a screw connection or a bayonet connection This simplifies the construction of the instrument, in particular also the assembly and dismantling, as is regularly necessary after and before an operation, in order to clean and sterilize the instrument.

A grip part is advantageously applied as a handle and is fixedly connected to the shank, so that the shank carries this grip part on the proximal side.

In order, on the one hand, to be able to vary the end of the hollow probe which projects beyond the shank, thus the distal end section which may be introduced into the cervical canal, with regard to its length, in order to be able to adapt to the anatomical requirements, but on the other hand, to be able to fix this in a reliable manner, so that it is connected to the grip part or to the shank in a rotationally fixed manner and also in a fixed manner in the axial direction, according to a further embodiment, one envisages the hollow probe being provided with locking recesses on the outer periphery and providing a spring-biased locking body within the grip part, in a manner such that this locking body engages into one of the recesses and thus, depending on the selection of the recess, fixes the axial extension of the hollow probe from the grip part or form the distal shank end and moreover with a positive fit. In order thereby to be able to grip the length of the distal end section of the hollow probe, which projects beyond the shank, from the outside in a simple manner, according to a further embodiment of the invention, the hollow probe is designed such that it proximally projects beyond the grip part and is provided with a scale there, which indicates the free length of the distal end section according to the axial position of the hollow probe. Thus with this design, at the proximal side one may read off from the instrument what length the distal end section has. This length of the distal end section, may also optionally be corrected or adapted even during the operation, since the locking mechanism is provided within the grip part.

According to an advantageous further embodiment of the invention, the hollow probe comprises a central suction channel which, in the end region of the shank via a transverse opening in the probe wall, runs out in an annular channel which is formed between the hollow probe and the shank, which is sealed by an O-ring and which runs to distally in the suction bell. The annular channel is connected via a hollow probe, which is conductively connected thereto, to a suction conduit. Such a suction conduit may connect on a corresponding connection union at the proximal end of the hollow probe, so that practically no conduits need to be led within the instrument, which is advantageous.

For illuminating the suction bell, in particular the distal-side peripheral ring, fiber-optics are arranged either in or on the shank, and these fiber optics run out at an end-face close to the inner periphery of the suction bell and are connected at the proximal side, via a fiber-optic cable, to a stationary light source. Instead, as is alternatively envisaged according to a further embodiment of the invention, light diodes or other suitable illumination means are provided in or on the suction bell and are supplied with electrical energy via electrical supply leads which are led in or on the shank.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a greatly simplified schematic representation, in a longitudinal section, of a uterus manipulator according to an embodiment of the invention;

FIG. 2 is an enlarged schematic sectional representation of the distal, proximal and middle parts of the instrument of FIG. 1;

FIG. 3 is a non-sectioned view of the instrument parts according to FIG. 2;

FIG. 4 is a greatly enlarged schematic representation, in section, of a middle section of the instrument in the region of the grip part;

FIG. 5 is a longitudinal section view of the distal instrument part in a first embodiment;

FIG. 6 is a sectional view through the shank of FIG. 5 in the distal end region;

FIG. 7 is a longitudinal section view, similar to FIG. 5, of another embodiment of the distal instrument part; and FIG. 8 is a sectional view, similar to FIG. 6, through the shank of FIG. 7 in the distal end region.

DETAILED DESCRIPTION OF THE INVENTION

The uterus manipulator represented by the Figures comprises a hollow probe 1, which extends through the whole instrument and at the distal end forms a distal end section 2, which is envisaged for introduction into a uterus through the cervical canal. The hollow probe 1 extends from the distal end section 2 proximally through a shank 3, which is fastened proximally in a grip part 4 forming the handle of the instrument. The hollow probe 1 extends through the grip part 4 and comprises a proximal end section 5, which projects beyond the grip part 4 on the proximal side and is designed in a hollow manner there. The hollow probe 1, however, is connected to the grip part 4 in a rotationally fixed manner, but in a releasable manner in the axial direction.

The length of the distal end section 2, thus the length with which the hollow probe 1 distally projects beyond the shank 3, may be adjusted, in order to be able to adapt the instrument, in particular the mentioned length, to the anatomical peculiarities of the patient. For this, a spring-biased locking body 6 is provided within the grip part 4, this locking body selectively being able to engage into one of a multitude of locking recesses 7, which are arranged over the length of the hollow probe 1 in the region of the grip part 4 (see FIG. 4). By pressing a button 8, provided on the grip part 4, against spring force, the locking body 6 in FIGS. 1 and 4 is moved downwards out of the locking recess 7, whereupon the hollow probe 1 is displaceable in the axial direction. After releasing the button 8, the locking body 6 locks into the next locking recess 7 which runs past, and specifically in a manner such that the hollow probe 1 is fixed in the grip part 4 with a positive fit, not only in the rotation direction but also in the axial direction. Here, markings 9 corresponding to the axial distance of the locking recesses 7 are provided on the proximal end section 5, and these markings are provided for example with sequential numbers, so that the operator may measure by these markings the length of the distal section 2 which is set therewith.

The hollow probe 1 over its whole length, thus also in the region of the shank 3 up to the distal end section 2, comprises a central suction channel 10 which runs out in a lateral and an end opening 11 at the distal end of the end section 2. This suction channel 10 in the region of the shank 3, and specifically roughly in the middle between the distal shank end and the grip part 4, is provided with a (not shown) recess in the wall, which connects this suction channel 10 to an annular channel 12, which is formed between the outer side of the hollow probe 1 and the shank 3, is sealed at the proximal side via an O-ring and is connected to a (likewise not shown) suction connection at the proximal end of the hollow probe, via which suction connection a conduit leading a vacuum may be connected. During the operation, a suctioning out of the uterus, thus of the cells which are released and which detach there, is effected via the previously described conduit connection.

In order to be able to securely guide the uterus, a suction bell 13 is provided at the distal end of the shank 3, and this is opened distally and is provided and envisaged for receiving the portio. The suction bell is designed in a stepped manner on its inner side, in order to comply with anatomical size differences. Two steps 14 are provided with the represented embodiments. Here, the suction bell 13 projects up to the shank 3, on which it is screw-fastened. In the base 15 of the suction bell 13, the annular channel 12 formed between the hollow probe 1 and the shank 3 runs out in an opening 16, via which the inner side of the suction bell 13 is connected to the suction connection of the instrument. The portio is not only pulled in to the suction bell 13 in a tight and firm manner by this, but moreover it is ensured that cells releasing there or cells which get between the distal end section 2 and the cervical channel, are securely sucked away. The hollow probe 1 is supported in the region of the distal end of the shank 3 by three pins 30 which are distributed symmetrically about the longitudinal axis, as is evident from the FIGS. 5 and 7.

Whereas the inner side of the suction bell 13 is designed in a stepped manner, the outer side is formed in a conically tapering manner. The suction bell 13 comprises a wall 17 which runs in a funnel-like manner and which is designed such that light which is fed in at the proximal end 18 of this wall 17 by total reflection, is led up to a distal ring 19, which during an operation illuminates the rear fornix and thus indicates to the operator that region which is to be laparoscopically severed from the other side, thus from the abdominal side. In particular, vessels lying in this region are visible through this distal ring 19. The feeding-in of light at the proximal end 18 is effected either by light diodes 20 (see FIG. 5) which are incorporated into the end of the wall 17 in a packed arrangement, or instead via fiber-optics 21 which end there, as are represented in FIG. 7.

The fiber-optics 21 are led through an annular channel which is formed between the shank 3 and an outer shank 22 surrounding this, and which ends in the grip part 4. There, the fiber-optics are led via a transverse channel 23 and a longitudinal channel 24, which connects thereto at 90°, longitudinally passes through the grip part and at whose end a fiber-optic connection 25 is provided. With the embodiment according to FIG. 5, instead of fiber-optics, electrical supply leads 26 are led through the previously described channels, via which supply leads the light diodes 20 are electrically supplied. A battery or a mains part may also be arranged in the grip part.

The suction bell 13, which is fastened at the end of the shank 3, is formed of transparent clear plastic, so that the operator may look through this and thus may introduce and place the instrument in a secure manner. At its outer periphery, roughly at the height of the fastening on the shank 3, the suction bell comprises a peripheral bead 27, which engages into a suitably designed groove of a sealing bell 28, which is formed of an elastic material, typically silicone, and is open proximally. The sealing bell 28 which, with its groove engages over the bead 27 with a positive fit, is designed widening in a proximal manner on the inside as well as outside, and ends in a peripheral sealing ring 29, the vaginal sealing ring. This sealing ring 29 seals the instrument with respect to the vaginal wall and ensures that on severing the rear fornix, the inner pressure (pneumoperitoneum) which is built up in the body interior for the purpose of laparoscopy, does not escape via the vagina. The sealing bell 28 may also consist of transparent plastic. The sealing bell 28 and the suction bell 13 form a unit which is fastened on the shank 3 via the suction bell 13 and which, as FIGS. 5 and 7 illustrate, is also supported on the outer shank 22 on the suction bell side. This unit is conceived as a disposable article, thus is kept ready in a sterile-packaged manner, is attached on the instrument before the operation, and is disposed of after the operation and after dismantling. Here, the suction bell 13 is designed in an intrinsically stiff manner, so that it behaves practically as a rigid component, wherein the sealing bell 28 is soft-elastic and bears on the vagina wall is a sealing manner.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A uterus manipulator for laparoscopically assisted vaginal hysterectomy comprising:
    a shank (3) having a distal end section (2) for introduction into a uterus through a cervical canal,
    a proximal handle (4),
    a distally open bell (13) for receiving a cervix, an inner surface of a sidewall of the distally open bell including at least two steps (14) along a longitudinal axis of the distally open bell,
    a vaginal sealing bell (28) arranged proximally with respect to the distally open bell (13),
    at least one suction channel (10), and
    at least one suction opening (11) in the distal end section (2),
    wherein the distally open bell defines a suction bell (13) and at least one suction channel (12) runs out in the suction bell (13),
    wherein the vaginal sealing bell (28) includes a proximally open end, an opposing distal end, and a sidewall extending therebetween, wherein the distal end, the proximally open end, and the side wall define a bell shape, the proximally open end having a sealing ring for forming a sealing bearing with a vaginal wall, and wherein the suction bell (13) and the vaginal sealing bell (28) form at least part of a unit which is releasably fastened on the shank (3).

2. The uterus manipulator according to claim 1, wherein illumination means (20; 21) are provided for illuminating a peripheral distal edge (19) of the suction bell (13).

3. The uterus manipulator according to claim 1, wherein the suction bell (13) is made of light-leading material, and includes a truncated-cone-shaped on an outside thereof, wherein light impingement is effected at an end-face (16) close to a shank-side inner periphery.

4. The uterus manipulator according to claim 1, wherein the unit comprises an intrinsically stiff component forming at least the suction bell (13) and a soft-elastic part forming at least the vaginal sealing bell (28).

5. The uterus manipulator according to claim 4, wherein the stiff component forming the suction bell (13) is a plastic injection molded part.

6. The uterus manipulator according to claim 1, wherein a hollow probe (1) is guided in the shank (3) in a rotationally fixed and axially displaceable manner, comprises the distal end section (2) for introduction into the cervical canal, and is fixable in at least two different axial positions with respect to the shank (3) or the proximal handle (4).

7. The uterus manipulator according to claim 6, wherein the hollow probe (1) comprises locking recesses (7) on an outer periphery thereof, and a spring-biased locking body (6) arranged in the grip part (4) engages into one of the recess (7) and thus fixes an axial extension of the hollow probe (1) from the grip part (4) and/or from the distal shank end.

8. The uterus manipulator according to claim 6, wherein the hollow probe (1) projects proximally beyond the proximal handle (4), and is provided with a scale (9), which indicates a free length of the distal end section (2) according to an axial position of the hollow probe (1).

9. The uterus manipulator according to claim 6, wherein the hollow probe (1) comprises a central suction channel (10) which in an end region of the shank (3), via a transverse opening in a probe wall, runs out into an annular channel (12) which is formed between the hollow probe (1) and the shank (3), is sealed by an O-ring, and connects at a proximal side thereof to a suction conduit.

10. The uterus manipulator according to claim 1, wherein the suction bell (13) unit is fastened on the shank close to a distal end thereof.

11. The uterus manipulator according to claim 1, wherein the shank (3) on a proximal side thereof carries a grip part (4) which forms a handle for the manipulator.

12. The uterus manipulator according to claim 1, wherein at least one fiber-optic (21) is arranged in or on the shank (3), the fiber-optic running out at an end-face (18) close to an inner periphery of the suction bell (13).

13. The uterus manipulator according to claim 1, wherein light diodes (20) are arranged in or on the suction bell (13) and at least one electrical supply lead (24) is led in or on the shank (3).

14. The uterus manipulator according to claim 1, wherein the sidewall of the vaginal sealing bell (28) being tapered from the proximal end toward the distal end.

15. The uterus manipulator according to claim 14, wherein the proximal end of the vaginal sealing bell (28) has a larger outer periphery than the distal end thereof.

* * * * *